US006635234B1

(12) United States Patent
Larsen et al.

(10) Patent No.: US 6,635,234 B1
(45) Date of Patent: Oct. 21, 2003

(54) PREPARATION AND USE OF RADIUM-223 TO TARGET CALCIFIED TISSUES FOR PAIN PALLIATION, BONE CANCER THERAPY, AND BONE SURFACE CONDITIONING

(75) Inventors: Roy H. Larsen, Bekkestua (NO); Gjermund Henriksen, Mjøndalen (NO); Øyvind S. Bruland, Hosle (NO)

(73) Assignee: Anticancer Therapeutic Inventions AS, Oslo (NO)

( * ) Notice: Subject to any disclaimer, the term of this patent is extended or adjusted under 35 U.S.C. 154(b) by 0 days.

(21) Appl. No.: 09/476,569

(22) Filed: Jan. 3, 2000

(30) Foreign Application Priority Data

Jan. 4, 1999 (NO) .......................................... 19990001

(51) Int. Cl.$^7$ .......................... A61K 51/00; A61K 51/02
(52) U.S. Cl. ...................... 424/1.11; 424/1.61; 424/1.69; 424/1.13; 424/1.21; 424/1.25; 424/1.29; 424/1.33; 424/1.73; 424/1.57; 424/1.53; 424/1.49; 424/1.45; 424/1.41; 424/1.37
(58) Field of Search ................................ 424/1.69, 1.11, 424/1.13, 1.21, 1.25, 1.29, 1.33, 1.37, 1.41, 1.45, 1.49, 1.53, 1.57, 1.61, 1.73

(56) References Cited

U.S. PATENT DOCUMENTS

| | | | | |
|---|---|---|---|---|
| 4,476,388 A | * | 10/1984 | Yakubovich et al. | ........ 250/366 |
| 4,970,062 A | * | 11/1990 | Atcher et al. | ................ 424/1.1 |
| 5,362,473 A | * | 11/1994 | Panek | ....................... 424/1.13 |
| 5,736,119 A | * | 4/1998 | Goldenberg et al. | ....... 424/1.53 |
| 5,809,394 A | | 9/1998 | Bray et al. | ...................... 423/3 |
| 6,117,413 A | * | 9/2000 | Fisher et al. | ................ 424/1.37 |

FOREIGN PATENT DOCUMENTS

| | | |
|---|---|---|
| WO | WO 93/09816 | 5/1993 |
| WO | WO 99/24081 | 5/1999 |

OTHER PUBLICATIONS

Introduction to Clinical Radiation Oncology, 2$^{nd}$ edition, 1997, Chapter 11 by Epstein et al , Genitourinary Tumors, pp. 314–319, and Chapter 17 by Cocia, Palliation, pp. 445–449.*
Reminton: The Science and Practice of Pharmacy, 19$^{th}$ edition, 1995, Chapter 51 by Chase et al, pp. 854–855.*
Pharmacotherapy, Elsevier, Dipiro et al, 1992, pp. 1294–1295.*
McDevitt et al., "Radioimmunotherapy with Alpha–Emitting Nuclides," Eur. J. Nucl. Med. 25:1341–1351 (1998).
Xiao–Hai, "Development of the Radiophamaceuticals for Interventional Tumor Therapy in China," Journal of Radioanalytical and Nuclear Chemistry 206:17–27 (1996).
Roy H. Larsen, et al., "$^{211}$At– and $^{131}$I–Labled Bisphosphonates with High in Vivo Stability and Bone Acumulation", Journal of Nuclear Medicine, 40, 1197–1203, (1999).

Chung K. Lee, et al., "Strontium–89 Chloride (Metastron) for Palliative Treatment of Bony Metastases: The University of Minnesota Experience", American J. Clinical Oncol, (CCT), 19(2): 102–107, (1996).
R.D. Lloyd et al., "Rn:Ra Ratios in Bone of Beagles Injected with $^{226}$Ra", Health Physics, vol. 60, pp. 567–568, (Apr. 1991).
R.D. Lloyd, et al., "Radium–224 Retention, Distribution, and Dosimetry in Beagles[1]", Radiation Research 92, 280–295 (1982).
B.A Muggenburg, et al., "The Biological Effects of Radium–224 Injected into Dogs [1]", Radiation Research 146, 176–186 (1996).
Walter A. Muller, "Studies of short–lived internal a–emitters in mice and rats", Int. J. Radiat. Biology, vol. 20, No. 1, 27–38, (1971).
Ole S. Nielsen, et al., "Bone Metastases: Pathophysiology and Management Policy", Journal of Clincal Oncology, vol 9, No. 3, pp. 509–524, (Mar. 1991).
Otto. G. Raabe, et al., "Skeletal Uptake and Lifetime Retention of $^{90}$Sr and $^{226}$Ra in Beagles [1]", Radiation Research 133, 204–218 (1993).
Mark A. Ritter, et al., "High–LET radiations induce a large proportion of non–rejoining DNA breaks", Nature, vol. 266, 14 (Apr. 1977).
J. Rundo, "The Radioactive Properties and Biological Behavior of $^{224}$Ra (ThX) and its Daughters*", Health Physics, vol. 35, pp. 13–20, (Jul. 1978).
Edward B. Silberstein, "Dosage and Response in Radiopharmaceutical Therapy of Painful Osseous Metastases" The Journal of Nuclear Medicine, vol. 37, No. 2, (Feb. 1996).
Chuanchu Wu, "An Improved Generator for the Production of $^{213}$Bi from $^{225}$Ac", Radiochimica Acta 79, 141–144 (1997).
R.W. Atcher, et al., "A Radionuclide Generator for the Production of $^{211}$Pb and its Daughters", J. Radioanal.Nucl. Chem., Letters 135, 3, 215–221, (1989).
Harold L. Atkins, et al., "Tin–117m (4+)–DTPA for Palliation of Pain from Osseous Metastases: A Pilot Study", Journal of Nuclear Medicine, 36:725–729, (1995).
Harold L. Atkins, "Overview of Nuclides for Bone Pain Palliation", App. Radiat. Isot. vol. 49, No. 4, pp. 277–283, (1998).
Micheal J. Blend, et al., "Radioimmunioscintigraphy in Patients with Early Stage Cutaneous malignant Melanoma", Journal of Nuclear Medicine, vol. 37, No. 2, (Feb. 1996).
J.M.H. de Klerk, et al., "Pharmacokinetics of Rhenium–186 After Administration of Rhenium–186 HEDP to Patients with Bone Metastases", Journal of Nuclear Medicine, vol. 33, No. 5, (May 1992).

(List continued on next page.)

Primary Examiner—Russell Travers
Assistant Examiner—S Sharareh
(74) Attorney, Agent, or Firm—Clark & Elbing LLP

(57) ABSTRACT

Processes for the preparation, prepared solutions, and the use of radium-223 for the treatment of calcified tumors, bone tumors, treatment of bones, bone surfaces and soft tissues is described.

20 Claims, No Drawings

OTHER PUBLICATIONS

Orthan Delikan, "Preparation of $^{224}$RA for Therapy of Ankylosing Spondylitis", *Health Physics,* vol. 35 pp. 21–24, (Jul. 1978).

Leif Spanier, et al., "Program to assist identifying and to list radioactivity gamma rays", *Evaluated Nuclear Structure Data File*, GDISP vers 1.2, (Jul. 1990).

Olav, Engebraaten, et al, "Site–Specific Experimental Metastasis Patterns of Two Human Breast Cancer Cell Lines in Nude Rats", *International Journal of Cancer*, 82, 219–225, (1999).

Ludwig E. Feinendegen, et al., "Alpha–Emitters fo Medical Therapy–Workshop of the United States Department of Energy", *Radiation Research*, 148, 195–201, (1997).

S. D. Fossa, et al., "Strontium in Bone metastases from hormone resistant prostate cancer: palition effect and biochemical changes", *Br. J. Cancer*, 66, 177–180, (1992).

I. Ross Garrett, "Bone Destruction in Cancer", *Seminars in Oncology*, vol. 20, No. 3, Suppl. 2, pp. 4–9, (Jun. 1993).

Eric J. Hall, "Linear Energy Transfer and Relative Biological Effectiveness", *Radiobiology for the Radiologist*, Fourth Edition, 153–164, (1994).

Sindre P. Hassfjell, "$^{212}$Pb/$^{212}$Bi–EDTMP–Synthesis and biodistribution of a novel bone seeking alpha–emitting radiopharmaceutical", *Journal of Labelled Compounds and Radiopharmaceuticals,* vol. XXXIV, No. 8, (1994).

S.P. Hassfjell, et al., "Bi–DOTMP—An Alpha Particle Emitting Bone Seeking Agent for Targeted Radiotherapy", *Nuclear Medical Biology*, 24, 231, (1997).

Roger W. Howell, et al., "Radiotoxicity of gadolinium–148 and Radium–223 in Mouse Testes: Relative Biological Effectiveness of Alpha–Particle Emitters in Vivo", *Radiation Research*, 147, 342–348 (1997).

J. A. Kanis, "Bone and Cancer: Pathophysiology and Treatment of Metastases", *Bone*, vol. 17, No. 2, Supplement (Aug. 1995).

* cited by examiner

PREPARATION AND USE OF RADIUM-223 TO TARGET CALCIFIED TISSUES FOR PAIN PALLIATION, BONE CANCER THERAPY, AND BONE SURFACE CONDITIONING

The present invention relates to the preparation and use of the "calcium analogue" alkaline-earth radionuclide radium-223 for the targeting of calcified tissues, e.g., bone and a physiological acceptable solution comprising $^{223}$Ra.

Biomedical use of radionuclides for pain palliation and/or cancer treatment, including prophylactic treatment of bone surfaces to slow down/inactivate undetectable metastases has previously been based upon β-emitters and conversion electron emitters.

A substantial percentage of cancer patients is affected by skeletal metastases. As many as 85% of patients with advanced lung, prostate and breast carcinoma develop bony metastases (Garret, 1993; Nielsen et al., 1991). Established treatments such as hormone therapy, chemotherapy and external radiotherapy often causes temporary responses, but ultimately most bone cancer patients experience relapses (Kanis, 1995). There is thus a strong need for new therapies to relieve pain and slow down tumor progression. Bone targeting radioisotopes has been included in clinical trials for the treatment of cancer to the skeleton (De Klerk et al., 1992, Fossà et al., 1992, Lee et al., 1996, Silberstein, 1996). These radiopharmaceuticals have been based on β-particle emitters (Atkins, 1998) and lately also a conversion electron ermitter (Atkins et al., 1995).Among these compounds which have so far been approved by US Food and Drug Administration, I.e. are strontium-89 (Metastron™) and $^{153}$Sm EDTMP (Lexidronam™). The strontium-89 compound can only be administered in amounts sufficient for pain palliation, not for tumor therapy, because a significant myelotoxicity occurs before significant antitumour therapeutic dose levels can be reached (Silberman, 1996).

Recently, one of the inventors authored a publication (Larsen et al., 1999) showing by dosimetry that α-emitters can be more advantageous than β-emitters as bone seekers. I.e. the shorter range of the α-emitters effecting less bone marrow exposure when the source is located at bone surfaces. In this study two β-emitting bisphosphonate bone seekers were compared with two β-emitting compounds with similar chemical structures and bone affinity. Dosimetric calculations indicated that, in mice, the bone surface to bone marrow dose ratios were approximately 3 times higher with the α-emitter compared to the β-emitter. This indicates that β-emitting bone seekers may have advantages over β- and/or electron emitting compounds because the radiation dose can be more strongly concentrated to the bone surfaces. Because of the short half life ($t_{1/2}$=7.2 h) and since its production is limited to only a few sites worldwide, astatine-211 is at present not yet available for large scale marketing. Besides astatine-211 only a few α-particle emitting radioisotopes are at present considered useful for biomedical applications (Feinendegen et al., 1997). The lead-212/bismuth-212 system has previously been used for preparation of bone seeking agents. Bismuth-212 complexed with ethylene-diamine-tetra(methylene-phosphonic acid) (EDTMP), or 1,4,7,10-tetraazacyclododecane 1,4,7,10-tetra (methylene-phosphonic acid) (DOTMP), showed a significant bone affinity. But because of the short half life of bismuth-212 ($t_{1/2}$=60.6 min), normal tissue exposure during the uptake phase of the radiopharmaceutical would be considerable (Hassfjell et al., 1994, 1997). This would be ever more pronounced with the other α-emitting bismuth isotope considered for biomedical use, the bismuth-213 (t½=46 min). Attempts have been made to use the β-emitter lead-212 ($t_{1/2}$=10.6 h) as an in vivo generator for $^{212}$Bi. However, a significant translocation affecting a high kidney accumulation of the α-emitter was observed (Hassfjell et al., 1997). Other α-emitting radioisotopes potentially useful for biomedical applications are the radium isotopes 224 and 226. As with other group II alkaline-earth metals, radium in its cationic state is a natural boneseeker.

Previously the radium isotopes 224 and 226 has been studied, partly because of their bone affinity (Loyd et al., 1982, 1991; Muggenburg et al., 1996, Müller, 1971; Raabe et al., 1993; Rundo, 1978). Radium-226 is, because of its long half-life (1600 years) and its noble gas radon-222 daughter ($t_{1/2}$=3.8 days), not considered useful for targeted radionuclide therapy. Because of its chemical nature, radon is inert to chemical bonding under in vivo conditions. It can therefore readily translocate in vivo when generated from the decay of the mother nuclide (Rundo, 1978). Inhaled radon mainly dissolves in body fluid and fat and is mainly eliminated from the body by exhalation (Rundo, 1978). In an experiment using bone samples, Lloyd and Bruenger (1991) reported that 89.5–94.25% of the radon-222 escaped from the bone after radium-226 had been administered to dogs. In contrast to radium-226, radium-224 has a half life ($t_{1/2}$=3.64 days) which seems very suitable for biomedical applications. $^{224}$Ra was used medically for many years to treat ankylosing spondylitis (Delikan, 1978). Unfortunately, also a significant fraction of the daughter isotopes of radium-224 escaped from bone, probably mainly because of the radon-220 ($t_{1/2}$ of 55.6 s) daughter (Lloyd et al., 1982; Müller et al., 1971; Rundo, 1978).

It is thus known from previous studies that when the radium isotopes $^{224}$Ra and $^{226}$Ra were incorporated in bone, a significant translocalisation of their radon daughters occurred, which could, at least partly, explain the known carcinogenic effect of these two radium isotopes. This may be one of the reasons why (α-emitters have not been evaluated clinically as bone seeking radiopharmaceutical against skeletal cancers.

It is the object of the present invention to provide a bone seeking radionuclide useful as a pharmaceutical agent, showing that radioactive decay products from its transformation do not translocalize significantly after its incorporation in bone (valid at least after 3 days from administration).

The present inventors made the significant and somewhat unexpected discovery that from $^{223}$Ra localized in bone, very little translocation of the radon daughter (as well as other radionuclides from the decay chain) occurred. Hence, the $^{223}$Ra series may be used to irradiate the bone surface without any significant translocation of radionuclides (including diffusion into bone marrow). Furthermore radium-223, should be more suitable as a boneseeking radiopharmaceutical since the half life (11.4 days) is about three times that of $^{224}$Ra, allowing a deeper incorporation into the matrix of the bone surfaces before decay occurs. Also, perhaps even more important, the radon daughter radon-219 has a short half-life (3.9 seconds), which should diminish translocation in, or as a result from the radon step. Three of the four β-particles emitted during decay of $^{223}$Ra and daughter nuclides are emitted immediately following $^{223}$Ra transformation (Seelman-Eggebert et al., 1981), i.e., of the first three transformations following $^{223}$Ra, the 3.9 second $^{219}$Rn alpha decay is the one with the longest half life (Table 1). The last α-emitter in the $^{223}$Ra chain, $^{211}$Bi ($t_{1/2}$=2.15 min) follows the decay of the β-emitter lead-211 ($t_{1/2}$=36.1 min) and may therefore show some translocation.

However, if the precursor, lead-211, is trapped inside of the bone matrix, also the last α-particle in the $^{223}$Ra series may be delivered to the bone surface area. In addition α-particles are high linear energy transfer (high-LET) radiation that is extremely cytotoxic to mammalian cells (Hall, 1994; Ritter et al., 1977). An α-particle emitting radiation source localized in target tissue can deliver radiation to a smaller target area, thus reducing normal tissue exposure compared to β-emitters.

The present invention relates to the preparation and the use of the "calcium analogue" alkaline-earth radionuclide radium-223 for the targeting of calcified tissues, e.g., bone and a physiological acceptable solution comprising $^{223}$Ra.

In this patent application the inventors have invented a novel use of $^{223}$Ra, i.e., as an α-emitting radiopharmaceutical for targeting of calcified tissues, e.g., bone surfaces and osseous tumor lesions. As indicated by the properties of the radionuclide(s) as well as the experimental examples presented in the present patent application, radium-223 can be suitable as a bone seeking radio-pharmaceutical. As an example, the invention may be used for prophylactic cancer treatment by delivering a focused dose to bone surfaces in patients with a high probability of having undetected micrometastases at bone surfaces. Another example of its potential use would be in the treatment of painful osseous sites in a similar fashion as the previously described β- and electron emitting radiopharmaceuticals for bone pain palliation.

Radium-223 localized onto the bone surfaces and/or in calcified tumors can, together with its daughter nuclides, deliver an intense and highly local dose of α-particles with less bone marrow dose compared to currently used β-emitting and/or electron emitting radiopharmaceuticals. Skeletal diseases, e.g., primary or metastatic cancer to the bone may be treated with the $^{223}$Ra radiopharmaceutical.

The present invention includes the use of the nuclide as a cationic species and/or associated to a chelator or another form of a carrier molecule with affinity for calcified tissues. This also includes, but are not limited to the combination of radium-223 with a chelator that can be subsequently conjugated to a molecule with affinity for calcified tissues. The intent is to use the radioisotope to generate a cascade of α-particles on bone surfaces and/or in calcified tumors for the palliation of pain caused by various diseases and/or for the prophylactic use against possible minimal disease to the skeleton, and/or also for the therapeutic treatment of established cancer to the bone. The diseases where the radioisotopes could be used includes, but are not limited to skeletal metastases of prostate-, breast-, kidney- and lung cancer as well as primary bone cancer and also multiple myeloma.

Radium-223 solutions are prepared for use in the targeting of calcified tissues or for bone surface irradiation. The following examples are showing a high and selective uptake of the $^{223}$Ra in bone with very little relocalization of daughter nuclides. This shows that bone surfaces can be sterilized to inactivate microscopical deposits of cancer cells and also that calcified cancerous lesions can be irradiated either for palliation or therapy with this isotope. The compound differs from other commonly used radiopharmaceuticals with bone affinity because the main dose component comes from α-particles which has a much shorter range compared to the frequently used beta and electron emitters. Therefore the dose delivered to red bone marrow can be significantly reduced with this new compound, i.e., myelotoxicity is likely to be reduced. Radium-223 differs from the previously used medical radionuclide radium-224 in the following: (1) $^{223}$Ra has a significantly longer half-life affecting better bone to soft tissue ratios because a significantly larger fraction of this isotope would be eliminated from the soft tissues before decay occurs. (2) Longer half life also allows a deeper incorporation of the radionuclide into the bone surfaces as the bone synthesis progresses, potentially improving retention of daughter isotopes which may otherwise translocate because of chemical diffusion and nuclear recoil. (3) Also the shorter half life of the $^{219}$Rn from $^{223}$Ra compared to the $^{220}$Rn from $^{224}$Ra, ensures less translocation of daughter nuclides from the $^{223}$Ra series.

The $^{223}$Ra salt or derivative thereof will be administered to a mammal, such as a human, in need thereof by all available administration routes, such as oral, subcutaneous, intravenous, intraarterial or transcutane. Preferably the active compound is administered by injection or infusion.

Oral administration is performed by use of tablets, capsules, powders or in liquid form, such as suspension, solution, syrup or emulsion. When formed into tablets conventional expicients, lubricating agents and binding agents are used. When administered as liquids conventional liquid carriers are used. When administered as injection or infusion solutions the carrier is preferably isotonic saline, with or without agent(s) to stabilize the radium cation to prevent precipitation of radium salts or insoluble complexes.

The active principle according to the invention could be used both in prophylactic, palliative and therapeutic treatment of non-malignant and malignant diseases affecting bones and soft tissues. The malignant diseases are selected from the group consisting of prostate cancer, breast cancer, kidney and urinary cancer, primary bone cancer, lung cancer and multiple myeloma, and the non-malignant disease are selected from the group consisting of autoimmune diseases affecting joints and skeleton, e.g. rheumatoid arthritis, schleroderma and spondyloartropathies.

The physiologically acceptable preparation for in vivo administration according to the present invention comprises dissolved radium-223 salt, with or without a single or a combination of several cations, as stabilizing alkaline earth metal cation analogue carrier, with or without an agent to prevent precipitation and/or generation of colloids, in addition to pharmacologically acceptable carriers and adjuvans. The cation acting as stabilizing alkaline earth metal cation can be selected from the group consisting of magnesium, calcium and strontium. Furthermore, the agent to prevent precipitation and/or generation of colloids is a carboxylic acid or a combination of carboxylic acids, such as oxalic acid, oxaloacetic acid, tartaric acid, succinic acid, malic acid and malonic acid. The concentrations of the compounds in the preparation will generally be less than the individual LD 50 dose, for example less than 20% of the LD 50 dose, and thus vary for the different components. The activity of $^{223}$Ra will be dependent upon the type and route of administration and the underlying condition or disease and-will vary between approximately 50 kBq to approximately 10 MBq, administered in single or multiple doses for mammals, such as for example humans.

According to the invention radium-223 is furthermore used to produce a pharmaceutically active preparation to treat non-malignant and malignant diseases affecting bone, bone surfaces and soft tissues, both palliative and therapeutically.

The preparation is administered to the mammal, such as humans or animals ,i.e. dogs, in need thereof, in a palliative or therapeutically effective amount.

According to the invention radium-223 can be used in a combination therapy, wherein the $^{223}$Ra preparation is combined with the following classes of treatment; chemotherapy including bisphosphonates, surgery, external beam irradiation, low-LET radiation emitting bone seeking radiopharmaceuticals, and hormonal treatment.

The invention is furthermore directed to a kit including $^{223}$Ra produced according to the inventive method, cations as stabilizing alkaline earth metal cation analogue carrier according and an agent to prevent precipitation and/or generation of colloids in addition to pharmaceutically acceptable carriers and suitable administration equipment.

In the following the present invention is described in detail by examples which in no way is intended to limit the scope of the invention as described by the enclosed claims.

Table 1 presents the physical properties of radium-223 and its daughter nuclides (Ekström et al., 1989). The decay of the $^{223}$Ra and its daughters causes the emissions of four α-particles. Such a cascade of α-particles can deliver a large radiation dose to a limited volume. Radium-223 therefore possesses extreme cytotoxicity, also compared to most α-emitters (Howell et al, 1997).

The following shows the Radium-223 and its daughters decay series (half life and mode of decay in brackets):

$^{223}$Ra (11.4 d., α) ⇒ $^{219}$Rn (3.9 s., α) ⇒ $^{215}$Po (1.8 ms., α) ⇒ $^{211}$Pb (36,1 min., β⁻) ⇒ $^{211}$Bi (2.15 min., α) ⇒ $^{207}$Tl (4,8 min., β⁻) ⇒ $^{207}$Pb(stable)

TABLE 1

| Nuclide | Emittance from $^{223}$Ra and daughters*. | | | | | |
|---|---|---|---|---|---|---|
|  | $^{223}$Ra | $^{219}$Rn | $^{215}$Po | $^{211}$Pb | $^{211}$Bi | $^{207}$Tl |
| α-Energy | 5.64 MeV | 6.75 MeV | 7.39 MeV |  | 6.55 MeV |  |
| β-Energy (max) |  |  |  | 0.47 MeV |  | 0.47 MeV |
| Energy Fraction.# | 0.207 | 0.248 | 0.271 | ≦0.017 | 0.24 | ≦0.017 |

*Data from Seelmann-Eggebert et al., 1981 and Ekstrøm et al., 1989
Relative to the total emitted energy for the complete decay chain.

The combined energy from the emitted radiation associated with the complete decay of $^{223}$Ra and daughters: ~27.5 MeV Fraction of energy emitted as (α-particles: ≧96%

Fraction of energy emitted as β-particles: ≦3%

Some gamma radiation (<0,3 MeV total) is also emitted during decay and can be used to determine the quality and quantity of isotopes in samples using gamma spectroscopy. E.g. radium-223 has a characteristic gamma peak at 154.19 keV (5.59% abundance), radon-219 has a peak at 401.78 keV (6,6%) and bismuth-211 has a 351.0 keV peak (12.8%) (Ekstrom et al., 1989). These can be used to determine if redistribution occurs for daughter isotopes in vivo. Also $^{223}$Ra has a 269.41 keV peak with 13.6% abundance, but this may be difficult to distinguish from a 271.23 keV peak, with 9.9% abundance of $^{219}$Rn.

Production methods has been described for Radium-223 (Atcher et al., 1989; Howell et al., 1997). $^{223}$Ra is a member of a natural radioactive family originating from U ($t_{1/2}$=7× 10$^8$ y.) via $^{231}$Th ($t_{1/2}$=25.6 y.) and the sequence $^{231}$Th→$^{231}$Pa ($t_{1/2}$=3.3×10$^4$ y.)→$^{227}$Ac ($t_{1/2}$=21.7 y.)→$^{227}$Th ($t_{1/2}$=18.7 d.)→$^{223}$Ra (11.4 d.). Atcher et al. (1989) used a cation exchange system (Bio-rad AG 50) to produce $^{223}$Ra from $^{227}$Ac. Howell et al. (1997) used the $^{226}$Ra (n,γ)$^{227}$Ra nuclear reaction to produce $^{223}$Ra. $^{227}$Ra ($t_{1/2}$=42 min) is rapidly transformed into $^{227}$Ac ($t_{1/2}$=21.77 years) which may be separated by different methods from the $^{226}$Ra target material. Howell et al (1997) separated the $^{227}$Ac chemically from a target solution. After that was $^{227}$Ac, together with its daughter products, transferred to an anion exchange column that retained $^{227}$Th, while the mother and daughter of this nuclide was eluted. Ten days later $^{223}$Ra could be eluted from the ion exchange column. If clinical batches were to be prepared by use of the generator principle, the application of ion exchange columns based on an organic backbone may be suboptimal because radiolysis may prevent long term multiple use of a radium generator based on this type of materials (Atcher et al., 1989).

Recently new materials have been developed, and are now commercial available, that are useful for separation of actinide radionuclides (selectivity for f-elements versus alkaline earth elements). These are based on silica particles covalently bound to or impregnated with active groups. Columns can be prepared using this material allowing the elution of some elements at conditions that can retain other elements. It would also be possible to use the active groups for the separation in wet/wet extraction systems using an organic and an aqueous phase.

EXAMPLES

In the following Example 1 $^{223}$Ra was produced. The novel method according to the invention for producing $^{223}$Ra for biomedical uses comprises both columns of inorganic matrix and liquid/liquid systems. A generator column containing a methane bis-phosphonic acid derivative on an inorganic matrix or the method can as well comprise a step of liquid/liquid extraction procedure in which one or more P,P' di-esterified methylene bis-phosphonic acid derivates are used as phase transfer agents.

In the method the generator column containing P,P' di-octyl methane bis-phosphonic acid on a silica matrix and the liquid/liquid extraction procedure is performed using P,P' di-octyl methylene bis-phosphonic acid or P,P' di(2-ethylhexyl) methane bis-phosphonic acid or combinations thereof as phase transfer agents. The prosedure with respect to the generator column is performed by using mineral acids which after neutralization is capable of giving physiologically compatible solutions of their salts, preferably nitric acid or hydrochloride acid. The concentration of said mineral acids being in the range of 0.01 to 8M, more preferably between 0.1 and 2M, most preferably between 0.5 and 1M. The liquid/liquid extraction step is performed using a water phase consisting of a mineral acid, preferably nitric acid or hydrochloric acid, the concentration of which being in the range of 0.01 to 8M, more preferably between 0.1 and 2M most preferably between 0.8 and 1.5M.

Example 1

$^{227}$Ac and $^{227}$Th were isolated from a $^{231}$Pa source prepared 27 years earlier (Sample was provided by Radiochemistry Group, Department of Chemistry, University of Oslo, Norway), by use of an f-element selective extraction chromatographic resin. The purified $^{227}$Ac and $^{227}$Th were subsequently adsorbed onto another f-element selective extraction chromatographic resin and used as a cow for $^{223}$Ra. The latter material has been used by Wu et al. (1997) for construction of a generator for $^{213}$Bi based on $^{225}$Ac.

Methods: A sample of the $^{213}$Pa source (with daughters) in an aqueous solution of 5 M $H_2SO_4$ and 1 M HF, was diluted 10 times with 1 M HCl. The solution was loaded onto a column of 3 mm inner diameter and length of 70 mm containing TRU-resin (EiChroM Industries, Darien, Ill., USA), which had been pre-equilibrated with 1 M HCl. $^{231}$Pa was retained on the column while $^{227}$Ac, $^{227}$Th, and $^{223}$Ra was eluted partly by the loading procedure and partly by washing the column with additional 10 ml of 1M HCl. After this a $^{223}$Ra generatior was prepared by using a modification of the column packing technique described by Wu et al. (1997). A 3×50 mm column of Silica Actinide Resin (EiChroM, Darien, Ill., USA) consisting of P,P' di-octyl methane bis-phosphonic acid (DIPEX, EiChroM Industries, Darien, Ill., USA) on silica particles with a diameter in the range of 20–50 μm was prepared and preconditioned with 1M HCl. Approximately one half of the resin was then removed from the column and mixed with the eluate from the TRU-resin column.

The eluate containing $^{227}$Ac. $^{227}$Th and $^{213}$Ra was thereafter loaded onto 3 mm i.d. and 50 mm long column containing Actinide-resin (Ac-resin) on 30–50 μm silica (EiCroM Industries, Darien Ill., USA). Briefly, the column had been prepared according to the method of Wu et al. (1997). After preconditioning the column with 1 M HCl, half of the material was removed and mixed with the eluate from the preceding step.

After 4 hours of gentle agitation at room temperature, the slurry containing the radionuclides was loaded onto the column. Finally, the column was washed with 5 ml of 1 M HCl. The column was retaining $^{227}$Ac and $^{227}$Th while $^{223}$Ra could be eluted with a few ml of either HCl or $HNO_3$, without any significant breakthrough of its parent and grandparent radionuclides. If desired, a subsequent purification step could be added by simply eluting the $^{223}$Ra eluate through a second AC-resin column to remove any traces of mother and grandmother nuclides. The HCl solution containing the $^{223}$Ra could be diluted in a buffer, sterile filtered and used as such. Alternatively, the purified $^{223}$Ra could be concentrated before use by loading the HCl solution onto a 2 mm i.d. and 25 mm long column containing a resin, e.g., AG 50W-X4-16 (Bio-Rad, Richmond, Calif., USA). Thereafter the $^{223}$Ra could be eluted nearly quantitatively by a small volume of 6 M $HNO_3$. The $HNO_3$ could thereafter be evaporated of and the residue could be resolved in a solution that could subsequently be sterile filtered.

Radioactivity quality and quantity measurements were performed either using Ge-detector (Canberra, Meriden, Conn., USA) combined with an amplifier and bias supply from EG&G Ortec (Oak Ridge, Tenn., USA) for gamma spectroscopy and/or a Canberra (model 7404-0 1 A) combined with an EG&G Ortec for alpha spectroscopy.

Results: In the TRU-resin column, $^{231}$Pa was quantitatively retained, i.e., the breakthrough was less than the detection limit of 0.5% compared to the daughter activity. Above 90% of the $^{227}$Ac and $^{223}$Th was collected in the eluate from the TRU-resin. For the AC-resin, multiple experiments indicated typical yields of 60–85 kBq $^{223}$Ra per 100 kBq of $^{227}$Th in the column (also named cow or generator) in the first few ml of stripping solution. The breakthrough of $^{227}$Ac and $^{227}$Th was determined to be less than (limited by detection capability) $4\times10^{-3}\%$ compared to $^{223}$Ra. It should be noted that the described separation methods could also be used with the $^{227}$Ac produced from $^{226}$Ra via $^{226}$Ra (n. γ) $^{227}$Ra→227Ac.

Conclusion: A set of methods is described for the production of $^{223}$Ra ensuring a high yield and a high purity useful for biological applications. Its distinction being the greater facilitation of routine production of clinically relevant activity levels of $^{223}$Ra from $^{227}$Ac. This is performed using a generator column based on a silica matrix (Wu et al., 1997) as compared to previously presented procedures involving more radiolytic sensitive ion-exchange resins containing organic matrixes (Atcher et al., 1989).

Example 2

The biodistribution of radium-223 prepared as described in Example 1 was studied.

Methods: Young male Balb/C mice with a body weight of 19–21 g were injected with 9 kBq of $^{223}$Ra in 150 μl of isotonic saline. Groups of five animals were sacrificed and dissected at 6 h and 3 days after injection. Sample weight was measured and samples were counted using (A) a "well type" NaI scintillation crystal (Harshaw Chemie BV, De Meern, Holland) combined with a Scaler Timer ST7 (NE Technology Ltd, Reading, UK) digital unit, (B) a Beckman LS 6500 (Beckman Instruments Inc. Fullerton, Calif., USA). Relative abundances of radionuclides were studied in blood, liver, kidney, and in standard samples with mother/daughter in equilibrium, using a Ge-detector (Canberra, Meriden, Conn., USA) combined with an amplifier and bias supply from EG&G Ortec (Oak Ridge, Tenn., USA).

Results: The biodistribution data is presented in Table 2. The data shows that $^{223}$Ra was selectively concentrated in bone compared to soft tissues. While all the soft tissue values were reduced between 6 h and 3 days after injection, the bone values increased with time. Femur to blood ratios increased from 129 to 691 from 6 h to 3 days. Spleen had the highest retention measured among the soft tissues, but the femur to spleen ratio also increased with time from 6.4 to 23.7 between 6 h and 3 days after injection.

TABLE 2

Biodistribution of radium-223 in Balb/C mice presented as % of injected dose per gram.

| Tissue | 6 hours | 3 days |
|---|---|---|
| femur | 25.86 ± 1.99 | 34.55 ± 7.87 |
| blood | 0.20 ± 0.23 | 0.05 ± 0.10 |
| kidney | 4.04 ± 0.33 | 0.38 ± 0.08 |
| liver | 0.89 ± 0.18 | 0.22 ± 0.32 |
| lung | 0.59 ± 0.56 | 0.06 ± 0.07 |
| muscle | 0.72 ± 0.39 | 0.30 ± 0.16 |
| heart | 0.10 ± 0.10 | 0.06 ± 0.07 |
| brain | 0.04 ± 0.01 | 0.12 ± 0.12 |
| spleen | 4.06 ± 1.4 | 1.46 ± 0.54 |
| small intestine | 0.79 ± 0.26 | 0.04 ± 0.03 |
| large intestine | 2.30 ± 0.60 | 0.13 ± 0.02 |

Based on gamma spectroscopy data no significant difference in relative distribution of radium-223 and its daughters, as determined by abundance of $^{211}$Bi, could be observed in the bone and most soft tissues. The ratio of $^{211}$Bi: $^{223}$Ra was in the spleen at the 6 hour point on average 54% compared to a standard solution. In liver and kidneys on the other hand, the $^{211}$Bi: $^{223}$Ra ratios in the samples were on the average 256 and 207% of the standards respectively. This indicates that some translocation occurred in the soft tissues. Also the $^{211}$Bi activity in soft tissues was in general very low compared to bone activity of this nuclide. The $^{211}$Bi in the soft tissues may have been generated from $^{223}$Ra present in soft tissues.

Conclusion: Excellent bone to normal tissue radioactivity ratios were obtained with $^{223}$Ra and daughters, indicating a significant potential for the targeting of calcified tissues with this radionuclide series.

Example 3

To examine if there was a difference in radioisotope retention between radium-223 and bismuth-211 in bone samples, gamma spectroscopic data for bone versus a standard solution with $^{223}$Ra and daughter radionuclides in equilibrium was studied.

Methods: Gamma spectroscopy with a germanium detector (Canberra, Meriden, Conn., USA) was performed on samples of femur from mice immediately after sacrificing and dissecting the animals. Samples of a standard solution of $^{223}$Ra and daughter radionuclides in equilibrium were studied. The distinct gamma peaks at 351.0 keV ($^{211}$Bi) and 154.2 keV ($^{223}$Ra) were used. A Localization Index (LI) was determined as follows:

$$LI=(B_{Bi}/S_{Bi})/(B_{Ra}/S_{Ra})$$

E.g., $B_{Bi}$–$^{211}$Bi count rate in bone; $S_{Ra}$–$^{223}$Ra count rate in standard Gamma spectra from five samples from the 6 h group and the 3 days group respectively were compared, to five and three samples from the standard solution respectively, using Student t-test for data columns.

Results: The LI values were on average 0.85 (P=0.059) at the 6 h point and 0.97 (P=0.749) at the 3 day point. However, the differences were not significant with respect to the P=0.05 level for the data sets.

Conclusion: Even for the radionuclide representing the fourth transformation in the series from $^{223}$Ra, the $^{211}$Pb-transformation, the retention in bone was similar to that of $^{223}$Ra.

Example 4

To study potential release of daughter isotopes after $^{223}$Ra was incorporated in bone, due to either nuclear recoil or diffusion processes, femurs from five animals killed 6 h, and 5 animals killed 3 days after injection were examined.

Methods: The bones were cleaved longitudinally, to expose the red marrow (spongious) areas, and thereafter cut into small fragments of less than 3 mg. Thereafter the samples were washed with Dulbeccos PBS (Sigma-Aldrich CO. LTD., Irvine, UK) using centrifugation. The supernatant was removed, mixed with scintillation liquid (Insta-Gel 11 plus, Packard BioScience BV, Groningen, The Netherlands) and counted on a scintillation counter (Beckman Instruments Inc. Fullerton, Calif., USA). After one day sample counting was repeated. A difference in counts after correcting for $^{223}$Ra decay between the two measurements was used as indication of release of daughter nuclide(s) from bone matrix.

Results: Animals killed after 6 hours showed some release of activity from bone. Compared to the total activity in bone an average of 1.8% was dissolved in PBS during washing. When the washing solutions were counted again after 12 h the activity then were only on average 0.2% of the bone sample. This indicates that some translocation of daughter isotopes had occurred but to a very small degree (probably for less than 2% of daughter isotopes). Animals killed after 3 days showed no significant counts compared to the background in the washing solution after washing. This indicates that if translocation occurred, it was below the detection limit, which was estimated to be less than 1% of the total bone radioactivity.

Conclusions: Based on the extractable radioactive fraction from finely fragmented bone samples it is indicated that daughter nuclide release (translocation) from bone matrix is low for the radium-223 series.

Example 5

It has been developed animal models with experimental metastasis pattern resembling those frequently observed in human patients (Engebraaten and Fodstad, 1999). One of these models consists of MT-1 cells injected intracardially into nude rats and is characterized by the consistent development of hind leg paralysis in the animals. Treatment (seven days after tumour cell inoculation) with the chemotherapeutics cisplatin or doxorubicin did not improve survival. Dissection and microscopic examination of the spine from animals affected by tumours revealed large masses of tumour cells replacing normal bone marrow and eroding the bony part of the spine.

The skeletal involvement in the above developed model made it suitable to demonstrate the therapeutic potential of $^{223}$Ra according to the invention against skeletal metastases.

Method: The therapeutic potential of radium-223 was studied in the MT-1/nude rat model where animals were inoculated with 1×106 MT-1 human breast cancer cells by injection into the left ventricle of the heart as described (Engebraaten and Fodstad,. 1999). These animals usually develop paralysis caused by growth of tumours in the spine. Groups of 4 and 5 animals each were then treated seven days later by receiving an intravenous injection of 200 µl of a vehicle solution without or with 10 kBq of radium-223 according to the invention.

Results: The group of four animals treated with vehicle solution alone experienced paralysis affected by tumour growth in the spine and was sacrificed between 20–25 days (means 22, 25 days) after tumour cell inoculation. In the group of five animals receiving vehicle solution containing $^{223}$Ra one animal had paralysis after 26 days, one after 40 days and one after 64 days while the two remaining animals lived throughout the experimental follow-up period of 90 days after tumour cell inoculation, without showing signs of paralysis.

Conclusion: $^{223}$Ra demonstrated a significant anti-tumour effect in animals with skeletal metastases.

References

Atcher R W, Friedman A M. Huizenga J R, Spencer R P. A radionuclide generator for the production of $^{211}$Pb and its daughter. J. Radioanal. *Nucl. Chem. Letters* 135, 215–221 (1989).

Atkins H L, Mausner L F, Srivastava S C. Meinken G E, Cabahug G E, D'Alessandro T. Tin-117 m(4+)DTPA for palliation of pain from osseous metastases: A pilot study. *J Nucl Med* 36, 725 (1995).

Atkins H L. Overview of nuclides for bone palliation. *Appl Radiat Isot* 49, 277–283 (1998).

De Kierk. J N M, van Dijk, A., van het Schip, A D, Zonnenberg, B A, and van Rijk, PP Pharmacokinetics of Rhenium-186 after administration of rhenium-186-HEDP to patients with bone metastases. *J Nucl Med* 33, 646–651 (1992).

Delikan O. Preparation of $^{224}$Ra for therapy of ankylosing spondylitis. Health Phys 35, 21–24 (1978).

Ekstrøm L, Spanier R. The EN SDF radioactivity data base for IBM-PC and computer network Access. Dept. Of Physics, University of Lund, Sweden (1989).

Engebraaten, O. and Fodstad, Ø. Site specific experimental metastasis patterns of two human breast cancer cell lines in nude rats. *Int. J Cancer* 82 (2), 219–225 (1999)

Feinendegen L E, McClure J J. Meeting Report. α-emitters for medical therapy-Workshop of the United States Department of Energy. Denver, Colo., May 30–31, 1996, *Radiat. Res.* 148, 195 (1997).

Fosså S D, Paus E, Lochoff M, Melbye R, Backe S, and Aas M. 89strontium in bone metastases from hormone resistant prostate cancer: Palliation effect and biochemical changes. *Br J Cancer,* 66, 177–180 (1992).

Garret R. Bone destruction in cancer. *Semin Oncol* 72, 3433–3435 (1993).

Hall E J. Radiology for the radiologist. Fourth edition, J B Lippincott Co. Philadelphia, s. 153–164 (1994).

Hassfiell S P, Hoff P, Bruland Ø S, Alstad J. $^{212}$Pb/$^{212}$Bi-EDTMP-Synthesis and biodistribution of a novel bone seeking alpha-emitting radiopharmaceutical. *J Labelled Compds Radiopharm* 34, 717–734 (1994).

Hassfjell, S P, Bruland, Ø S, Hoff, P. $^{212}$Bi-DOTMP- An alpha particle emitting bone seeking agent for targeted radiotherapy. *Nucl Med Biol* 24, 231–237 (1997).

Howell R W, Goddu S M, Narra V R, Fisher D R, Schenter R E, Rao D V. Radio-toxicity of Gadolinium-148 and radium-223 in mouse testes. Relative biological effectiveness of alpha-particle emitters in vivo. *Radial Res* 147, 342–348 (1997).

Kanis J A. Bone and cancer. Pathophysiology and treatment of metastases. *Bone* 17, 101 s–105 s (1995).

Larsen R H, Murud K M, Akabani G, Hoff P, Bruland Ø S, Zalutsky N I R. $^{211}$At- and $^{131}$I-labeled bisphosphonates with high in vivo stability and bone accumulation. *J Nucl Med* 40, 1197–1203 (1999).

Lee C K, Aeppli D M, Unger J, Boudreau R J, Levitt S H. Strontium-89 chloride (Metastron) for palliative treatment of bony metastases: The University of Minnesota experience. *Am J Clin Oncol* 19, 102–107 (1996).

Lloyd R D, Bruenger F W, Rn:Ra ratios in bone of beagles injected with $^{226}$Ra. *Health Phys.* 60, 567–568 (1991).

Lloyd R D, Mays C W, Taylor G N, Atherton D K Bruenger F W, Jones C W. Radium-224 retention, distribution, and dosimetry in beagles. *Radial Res* 92, 280–295 (1982).

Muggenburg B A, Hahn, F F, Griffith Jr W C, Lloyd R D, Boecker B B. The biological effects of radium-224 injected into dogs. *Radiat Res* 146, 171–186 (1996).

Müller W A. Studies on short-lived internal α-emitters in mice and rats Part I. $^{224}$Ra. *Int J Radiat Biol* 20, 27–38 (1971).

Nielsen, O S, Munro A J, Tannock I F. Bone metastases: Pathophysiology and management policy. *J Clin Oncol* 9, 509–524 (1991).

Raabe O G, Parks N J. Skeletal uptake and lifetime retention of Sr-90 and Ra-226 in beagles. *Radial Res* 133, 204–218 (1993).

Ritter M A, Cleaver J E, Tobias C A. High-LET radiations induce a large proportion of nonrejoining DNA breaks. *Nature,* 266, 653–655 (1977).

Rundo J. The biological behaviour of 224Ra (ThX) and its daughters. *Health Phys* 35, 13–20 (1978).

Seelmann-Eggebert W, Pfennig G, Münzel H, Klewe-Nebenius H. Nuklidkarte, Kernforschungszentrum Karlsruhe (1981).

Silberstein E B. Editorial:Dosage and response in radiopharmaceutical therapy of painful osseous metastases.1. *Nuel. Med.*, 37, 249–252 (1996).

Wu C, Brechbiel M W, Gansow O A. An improved production of $^{213}$Bi from $^{225}$Ac. *Radiochimica Acta* 79, 141–145 (1997).

What is claimed is:

1. A method for the prophylactic or therapeutic treatment of a metastasis from a soft tissue tumor to a bone in a mammal, said method comprising administering to the mammal in need therof, a therapeutically or prophylactically effective amount of a free metallic cation of the alkaline earth metal radium-223.

2. A method as claimed in claim 1 wherein radium-223 is administered as a salt in solution.

3. The method of claim 2, wherein said method further comprises co-administering a further alkaline earth metal cation.

4. A method as claimed in claim 3 wherein said further cation is selected from the group consisting of magnesium, calcium and strontium.

5. A method as claimed in claim 2 wherein there is co-administered an agent serving to prevent precipitation of radium-223.

6. A method as claimed in claim 2 wherein there is co-administered an agent serving to prevent colloid generation.

7. A method as claimed in claim 1 wherein said mammal is a human.

8. A method a claimed in claim 1 wherein said amount is a therapeutically effective amount.

9. A method as claimed in claim 1 wherein said amount is prophylactically effective amount.

10. The method of claim 1, wherein said method is used to treat a metastasis resulting from a malignant disease selected from the group consisting of prostate cancer, breast cancer, kidney and urinary tract cancers, lung cancer, and multiple myeloma.

11. The method of claim 1, wherein said method further comprises administering to said mammal a therapeutic treatment selected from the group consisting of chemotherapy, surgery, external beam irradiation, low linear energy transfer radiation emitting bone-seeking radio-pharmaceutical treatment, hormonal treatment, and a combination therapy comprising radium-223 and a bisphosphonate.

12. A method as claim in claim 5 or claim 6 wherein there is co-administered a carboxylic acid.

13. A method as claimed in claim 12 wherein said carboxylic acid is selected from the group consisting of oxalic, oxaloacetic, tartaric, succinic, malic and malonic acids.

14. A method as claimed in claim 1 wherein said radium-223 is administered by injection.

15. A method as claimed in claim 1 wherein said radium-223 is administered by infusion.

16. A method as claimed in claim 1 wherein said radium-223 is administered by ingestion.

17. The method of claim 1, wherein said therapeutically or prophylactically effective amount is in the range 50 kBq to 10 MBq.

18. The method of claim 1, wherein said administering is carried out by an intravenous or an intraarterial route.

19. The method of claim 1, wherein said metastasis is on a surface of said bone.

20. The method of claim 1, wherein said administering is systemic administering.

* * * * *

UNITED STATES PATENT AND TRADEMARK OFFICE
CERTIFICATE OF CORRECTION

PATENT NO. : 6,635,234 B1
DATED : October 21, 2003
INVENTOR(S) : Roy H. Larsen, Gjermund Henriksen, and Øyvind S. Bruland It is certified that error appears in the above-identified patent and that said Letters Patent is hereby corrected as shown below:

Title page,
Item [56], References Cited, OTHER PUBLICATIONS, "Reminton" reference, replace "Reminton" with -- Remington --.

Column 1,
Line 29, replace "ermitter" with -- emitter --;
Line 43, replace "β-emitting bisphosphonate" with -- α-emitting bisphosphonate --; and
Line 49, replace "β-emitting bone seekers" with -- α-emitting bone seekers --.

Column 2,
Line 2, replace "t½" with -- $t_{½}$ --.

Column 3,
Line 14, delete "application".

Column 4,
Line 19, replace "expicients" with -- excipients- --;
Lines 33-34, replace "schleroderma" with -- scleroderma --;
Line 34, replace "spondyloartropathies" with -- spondyloarthropathies --; and
Line 41, replace "adjuvans" with -- adjuvants --.

Column 6,
Line 52, replace "prosedure" with -- procedure --; and
Line 66, replace "$^{23}1Pa$" with -- $^{231}Pa$ --.

Column 7,
Line 17, replace "generatior" with -- generator --; and
Line 27, replace "$^{213}Ra$" with -- $^{223}Ra$ --.

Column 8,
Line 6, replace "227Ac" with -- $^{227}Ac$ --.

Column 9,
Line 29, replace "$B_{Bi}$-$^{211}Bi$" with -- $B_{Bi}=^{211}Bi$ --; and
Line 29, replace "$S_{Ra}$-$^{223}Ra$" with -- $S_{Ra}=^{223}Ra$ --.

Column 10,
Line 32, replace "1×106" with -- $1×10^6$ --.

UNITED STATES PATENT AND TRADEMARK OFFICE
CERTIFICATE OF CORRECTION

PATENT NO. : 6,635,234 B1
DATED : October 21, 2003
INVENTOR(S) : Roy H. Larsen, Gjermund Henriksen, and Øyvind S. Bruland It is certified that error appears in the above-identified patent and that said Letters Patent is hereby corrected as shown below:

Column 12,
Line 11, replace "therof" with -- thereof --; and
Line 46, replace "claim" with -- claimed --.

Signed and Sealed this

Twenty-fourth Day of August, 2004

JON W. DUDAS
*Director of the United States Patent and Trademark Office*